US008038647B2

(12) United States Patent
Harding et al.

(10) Patent No.: US 8,038,647 B2
(45) Date of Patent: Oct. 18, 2011

(54) NEEDLE SAFETY DEFLECTION DEVICE

(75) Inventors: Weston F. Harding, Lehi, UT (US);
Austin Jason McKinnon, Herriman, UT (US); Wan Suwito, Sandy, UT (US);
Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 110 days.

(21) Appl. No.: 12/124,733

(22) Filed: May 21, 2008

(65) Prior Publication Data
US 2009/0292243 A1 Nov. 26, 2009

(51) Int. Cl.
*A61M 5/00* (2006.01)
(52) U.S. Cl. ...................................... 604/110
(58) Field of Classification Search .................. 604/110, 604/164.12, 164.08, 198, 263, 192, 158, 604/162; 600/573; 128/919
See application file for complete search history.

(56) References Cited

U.S. PATENT DOCUMENTS

| | | | |
|---|---|---|---|
| 4,978,344 A | 12/1990 | Dombrowski et al. | |
| 5,137,515 A | 8/1992 | Hogan | |
| 5,304,136 A | 4/1994 | Erskine et al. | |
| 5,456,668 A | 10/1995 | Ogle, II | |
| 5,584,810 A * | 12/1996 | Brimhall | 604/110 |
| 5,879,331 A | 3/1999 | Osterlind | |
| 5,951,515 A | 9/1999 | Osterlind | |
| 5,957,887 A * | 9/1999 | Osterlind et al. | 604/110 |
| 5,997,507 A | 12/1999 | Dysarz | |
| 6,193,690 B1 | 2/2001 | Dysarz | |
| 6,203,527 B1 | 3/2001 | Zadini et al. | |
| 6,287,278 B1 | 9/2001 | Woehr et al. | |
| 6,629,959 B2 * | 10/2003 | Kuracina et al. | 604/192 |
| 7,179,244 B2 * | 2/2007 | Smith et al. | 604/110 |
| 7,182,734 B2 * | 2/2007 | Saulenas et al. | 600/573 |
| 2004/0049155 A1 | 3/2004 | Schramm | |
| 2004/0092889 A1 | 5/2004 | Ferguson et al. | |
| 2004/0243060 A1 | 12/2004 | Rossi et al. | |
| 2006/0264828 A1 * | 11/2006 | Woehr et al. | 604/110 |

FOREIGN PATENT DOCUMENTS
FR 2 867 083 A1 9/2005
WO 2006062983 A1 6/2006

* cited by examiner

*Primary Examiner* — Nicholas D Lucchesi
*Assistant Examiner* — Brooke Matney
(74) *Attorney, Agent, or Firm* — Mony R. Ghose; Kirton & McConkie

(57) ABSTRACT

An apparatus to automatically secure an end of a needle after contact with a blood vessel. The apparatus may include a housing and a biasing member, where the housing includes a hollow interior region extending between a proximal end and a distal end thereof. A proximal opening may be integrated into the proximal end, while a distal opening may be integrated into the distal end. The proximal and distal openings may be configured to receive a needle therethrough along a longitudinal axis. The biasing member may be coupled to the housing and configured to apply a force to the needle. The force may be oriented to displace the needle relative to the longitudinal axis upon retracting an end of the needle through the distal opening into the hollow interior region. Embodiments of the present invention may thus secure the end of the needle within the hollow interior region after use to prevent accidental needle sticks and exposure to blood and bloodborne pathogens.

19 Claims, 7 Drawing Sheets

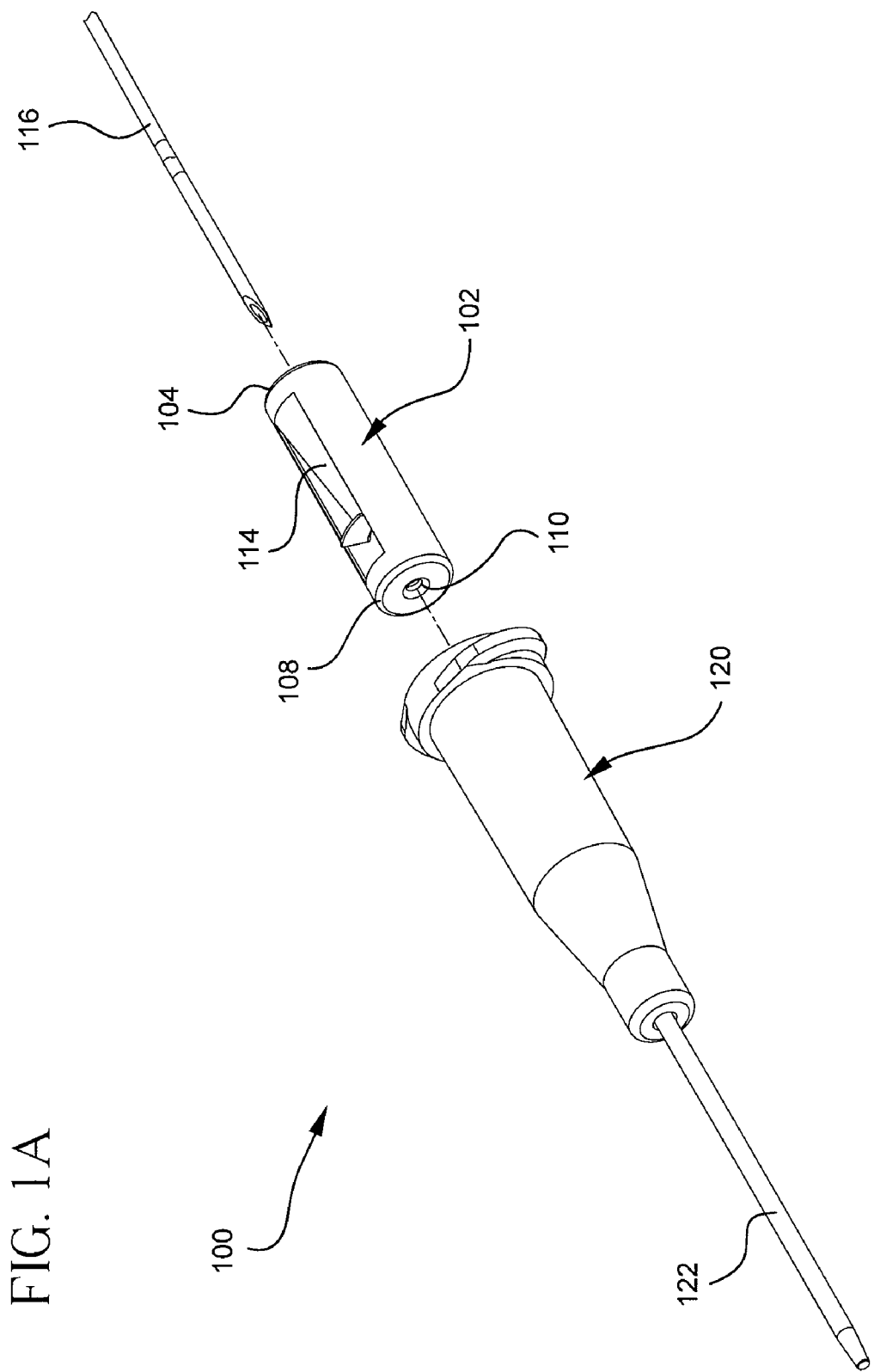

NEEDLE SAFETY DEFLECTION DEVICE

BACKGROUND OF THE INVENTION

Hypodermic needles are notorious for spreading blood-borne diseases such as Hepatitis B, Hepatitis C, and Human Immunodeficiency Virus ("HIV"), the virus that causes Autoimmune Deficiency Syndrome ("AIDS"). Health care workers are among those most at risk for contracting such diseases, as hypodermic needles are commonly used in medical fields. Needle stick injuries may arise during planned use and exposure, and/or as a result of carelessly or maliciously discarded needles.

The Federal Needle Stick Safety Act was enacted into law on Nov. 6, 2000, and is aimed at reducing the risk to health care workers arising from accidental needle sticks. Among other compliance mandates, the Federal Needle Stick Safety Act requires the use of needles with engineered needle injury protections. Accordingly, many hypodermic needles manufactured today include a needle tip shield or the like to protect against accidental needle sticks.

Of particular concern, however, are injuries from hollow-bore needles, especially those used for blood collection or intravenous ("IV") catheter insertion. These devices are likely to contain residual blood and are associated with an increased risk for HIV transmission. Additionally, devices that require manipulation or disassembly after use, such as hollow-bore needles used for IV catheter insertion, have rates of injury over five times that for disposable hypodermic syringes. Such injuries most often occur during or after use and before disposal of the used needle.

IV catheters are traditionally used to infuse fluids, such as saline solution, various medicaments, and/or total parenteral nutrition into a patient. Such catheters may also be used to withdraw blood from a patient, and/or monitor various parameters of the patient's vascular system.

To introduce an IV catheter into a patient, an over-the-needle catheter may be mounted over a hollow-bore introducer needle having a sharp distal tip. The inner surface of the catheter may tightly engage the outer surface of the needle to prevent catheter peelback and facilitate insertion of the catheter into a blood vessel. The tip of the introducer needle may extend beyond the distal tip of the catheter to enable insertion of the catheter at a shallow angle through the patient's skin and into a blood vessel.

To verify proper placement of the needle and catheter in the blood vessel, the clinician may confirm the presence of "flashback" blood in a flashback chamber associated with the catheter and needle assembly. Once proper placement is confirmed, the clinician may then apply pressure to the blood vessel to occlude the vessel, thereby minimizing further blood flow through the introducer needle and catheter. The clinician must then withdraw the needle from the catheter to enable continued access to the blood vessel through the catheter. This process of physically manipulating and disassembling the needle and catheter after the catheter has been properly positioned creates substantial risks of accidental needle sticks and exposure to blood and blood-borne pathogens.

From the foregoing discussion, it should be apparent that a need exists for a safety device integral to an intravenous catheter assembly to prevent injury from accidental needle sticks and exposure to biological contaminants after the catheter has been positioned in a blood vessel. Beneficially, such a safety device would enable simple and effective operation, minimize an amount of physical manipulation needed to disassemble the catheter assembly after use, and ensure that the needle tip is properly secured prior to such disassembly. Such a safety device is disclosed and claimed herein.

SUMMARY OF THE INVENTION

The present invention has been developed in response to the present state of the art, and in particular, in response to the problems and needs in the art that have not yet been met by currently available safety devices for intravenous catheter assemblies. Accordingly, the present invention has been developed to provide a safety device integral to an intravenous catheter assembly that overcomes many or all of the above-discussed shortcomings in the art.

An apparatus to automatically secure an end of a needle after contact with a blood vessel in accordance with embodiments of the present invention may include a housing and a biasing member. The housing may include a hollow interior region extending between a proximal end and a distal end of the housing. A proximal opening may be integrated into the proximal end of the housing, while a distal opening may be integrated into the distal end. The proximal and distal openings may be configured to receive a needle therethrough along a longitudinal axis. In some embodiments, the needle may include a securing feature to prevent withdrawing an end of the needle through the proximal opening.

The biasing member may be coupled to the housing and configured to apply a force to the needle. The force may be oriented to displace the needle relative to the longitudinal axis upon retracting an end of the needle through the distal opening into the hollow interior region. In certain embodiments, the hollow interior region may include a retention element to retain the end of the needle in a position displaced from the longitudinal axis. An urging element communicating with the needle may urge the end of the needle into a position where it may be retained by the retention element. Embodiments of the present invention may thus secure the end of the needle within the hollow interior region after use.

In certain embodiments, the apparatus may further include a catheter adapter to receive at least a portion of the housing and direct the needle into a catheter extending therefrom. A latch member may secure the catheter adapter to the housing. In one embodiment, the latch member communicates with the biasing member such that the latch member releases the catheter adapter from the housing upon retracting the end of the needle through the distal opening. The latch member may be integrated with the biasing member, and/or may selectively protrude through an opening in the housing to engage an aperture in the catheter adapter to secure the catheter adapter to the housing.

In some embodiments, the apparatus may further include a lock feature to substantially lock a position of the biasing member relative to the hollow interior region to maintain displacement of the needle when the end of the needle is retracted through the distal opening. The lock feature may include a hook in the hollow interior region to engage at least a portion of the biasing member to maintain displacement of the needle. In certain embodiments, the lock feature may be integrated with the biasing member such that the lock feature selectively abuts a wall of the hollow interior region to maintain displacement of the needle.

A method to secure an end of a needle in accordance with embodiments of the present invention is also presented. The method may include providing a housing having a proximal end, a distal end, and a hollow interior region extending therebetween. A proximal opening may be integrated into the proximal end of the housing and a distal opening may be integrated into the distal end, such that the proximal and distal openings may receive a needle therethrough along a longitudinal axis.

A biasing member may be coupled to the housing and configured to apply a force to the needle. The force may be oriented to displace the needle relative to the longitudinal axis upon retracing an end of the needle through the distal opening into the hollow interior region, thereby securing the end of the needle within the hollow interior region.

In certain embodiments, the method may include inserting the needle through the proximal and distal openings along the longitudinal axis. In other embodiments, the method may include providing a catheter adapter to receive a portion of the housing and direct the needle into a catheter extending therefrom. The catheter adapter may be secured to the housing via a latch member. In some embodiments, the latch member may be associated with the biasing element such that the latch member releases the catheter adapter from the housing upon retracting the end of the needle through the distal opening. In still other embodiments, a lock feature may communicate with the biasing element to substantially lock a position of the biasing member relative to the hollow interior region upon retracting the end of the needle through the distal opening.

An intravenous catheter assembly to automatically secure an end of a needle after contact with a blood vessel in accordance with the present invention may include piercing means for piercing a blood vessel to acquire intravenous access, housing means for housing at least a portion of the piercing means, and biasing means for applying a force to the piercing means. The housing means may include a hollow interior region extending between a proximal end and a distal end thereof. The proximal end of the housing means may include a proximal opening, and the distal end may include a distal opening. The proximal and distal openings may be configured to receive the piercing means therethrough along a longitudinal axis.

The biasing means may be configured to apply a force oriented to displace the piercing means relative to the longitudinal axis. This force may be applied upon retracting an end of the piercing means through the distal opening into the hollow interior region, thereby securing the end of the piercing means within the hollow interior region.

In certain embodiments, the intravenous catheter assembly may further include latch means for securing a catheter adapter to the housing means. The latch means may communicate with the biasing means such that the force applied to the piercing means causes the latch means to release the catheter adapter from the housing means.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 1a is an exploded perspective view of a safety device integral to an intravenous catheter assembly in accordance with certain embodiments of the present invention;

DETAILED DESCRIPTION

The illustrated embodiments of the present invention will be best understood by reference to the drawings, wherein like parts are designated by like numerals throughout. It will be readily understood that the components of the present invention, as generally described and illustrated in the Figures herein, may be arranged and designed in a wide variety of different configurations. Thus, the following more detailed description, as presented in the Figures, is not intended to limit the scope of the invention as claimed, but is merely representative of selected embodiments of the invention. The following description is intended only by way of example, and simply illustrates certain selected embodiments of devices, systems, and processes that are consistent with the invention as claimed herein.

As used in this specification, the term "needle" refers to any of various devices that may be used to pierce the skin to acquire intravenous access, such as a hypodermic needle, a hollow-bore needle, a surgical knife, and the like. The term "catheter adapter" refers to a medical device providing fluid communication and mechanical connection between an intravenous catheter and another vascular access device, such as a needle safety device, syringe, or the like.

Figure 1B:
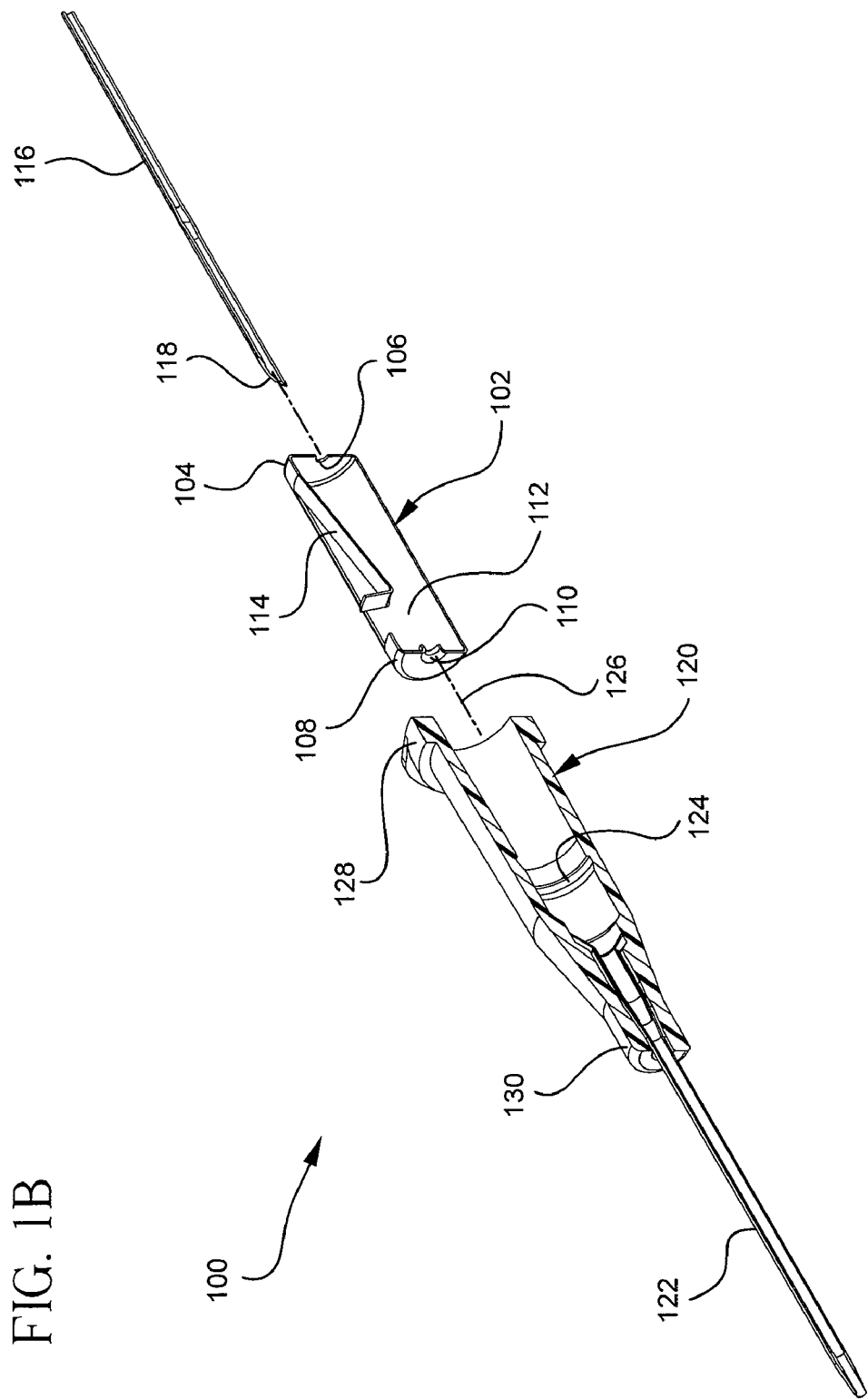
FIG. 1b is an exploded cross-sectional view of a safety device integral to an intravenous catheter assembly in accordance with certain embodiments of the present invention.

Referring now to FIG. 1, an intravenous catheter assembly 100 in accordance with the present invention may include a housing 102, a catheter adapter 120, and a needle 116. The housing 102, catheter adapter 120, and needle 116 may align with each other along a longitudinal axis 126, and may be adapted for assembly as discussed in more detail below.

The housing 102 may be longitudinally oriented around the longitudinal axis 126 and may include a proximal end 104, a distal end 108, and a hollow interior region 112 extending therebetween. A proximal opening 106 may be integrated into the proximal end 104 and may be substantially aligned with a distal opening 110 integrated into the distal end 108. The proximal and distal openings 106, 110 may be configured to receive the needle 116 therethrough along the longitudinal axis 126. The housing may further include a biasing member 114 to apply a force to the needle 116, as discussed in more detail below.

The needle 116 may include an outer circumference at least slightly less than the inner circumferences of the proximal and distal openings 106, 110. The needle tip 118 may be introduced into the proximal opening 106 of the housing and the needle 116 advanced through the hollow interior region 112 to exit the distal opening 110. In this manner, the needle 116 may extend from the proximal opening 106 to the distal opening 110 along the longitudinal axis 126. In some embodiments, the proximal and distal openings 106, 110 may include substantially smooth surfaces to facilitate manipulation of the needle 116 therethrough.

The catheter adapter 120 may include an internal diameter at least slightly larger than an outer diameter of the housing 102, such that the proximal end 128 of the catheter adapter 120 may receive at least the distal end 108 of the housing 102. In certain embodiments, the catheter adapter 120 may receive a substantial portion or an entire length of the housing 102. The connection between the catheter adapter 120 and the housing 102 may provide fluid communication and a mechanical seal therebetween. In some embodiments, the connection between the catheter adapter 120 and the housing 102 may be provided by a threaded connection, a press fit, or by any other means or device known to those in the art.

In one embodiment, an outer surface of the housing 102 and/or catheter adapter 120 may be substantially cylindrical and molded along the longitudinal axis 126 to provide a secure, comfortable grip. In some embodiments, for example, the housing 102 or catheter adapter 120 may include grooves, ridges or an otherwise textured outer surface to facilitate a secure grip.

The catheter adapter 120 may include a catheter 122 extending from a distal end 130 thereof. The catheter 122 may be integral to the catheter adapter 120 or coupled thereto. The catheter adapter 120 and catheter 122 may cooperate to guide the needle 116 therethrough such that the needle tip 118 may protrude through the catheter 122 to facilitate an intravenous catheterization process. Likewise, the needle 116 may be selectively retracted from the catheter 122 and catheter adapter 120 after use.

In some embodiments, as discussed in more detail below, the catheter adapter 120 may include an aperture 124 or other securing feature to facilitate securing the housing 102 to the catheter adapter 120. For example, a latch member (not shown) coupled to the housing 102 may extend through an opening (not shown) in the housing 102 to engage the aperture 124, thereby securing the housing 102 to the catheter adapter 120.

Figure 2:
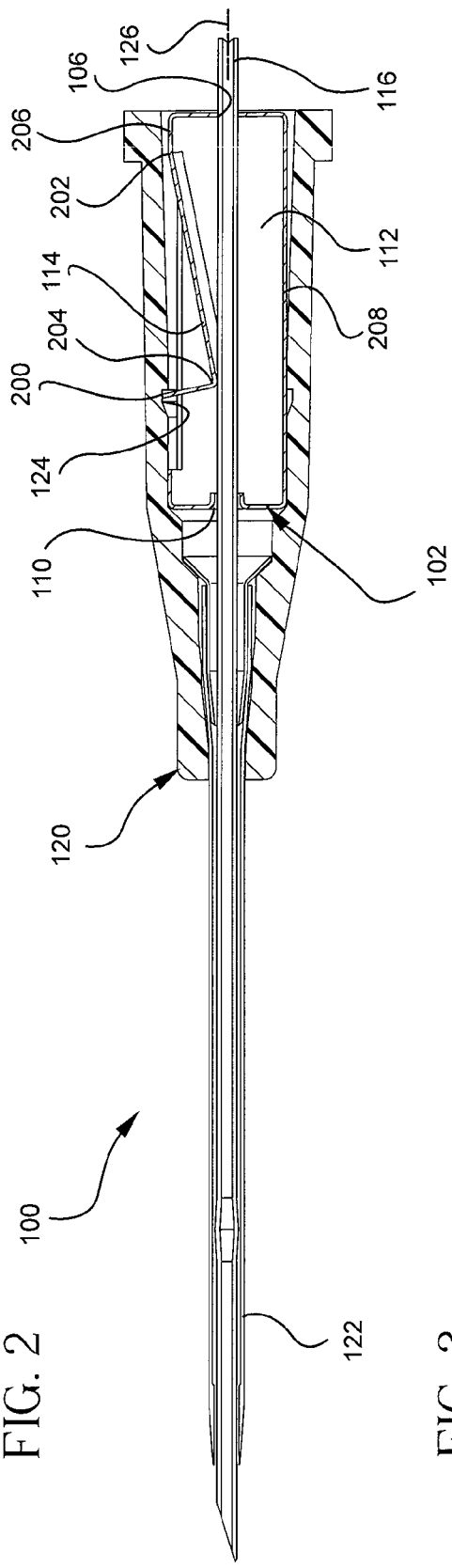
FIG. 2 is a cross-sectional view of one embodiment of a safety device integrated into an intravenous catheter assembly in accordance with the present invention.
Figure 3:
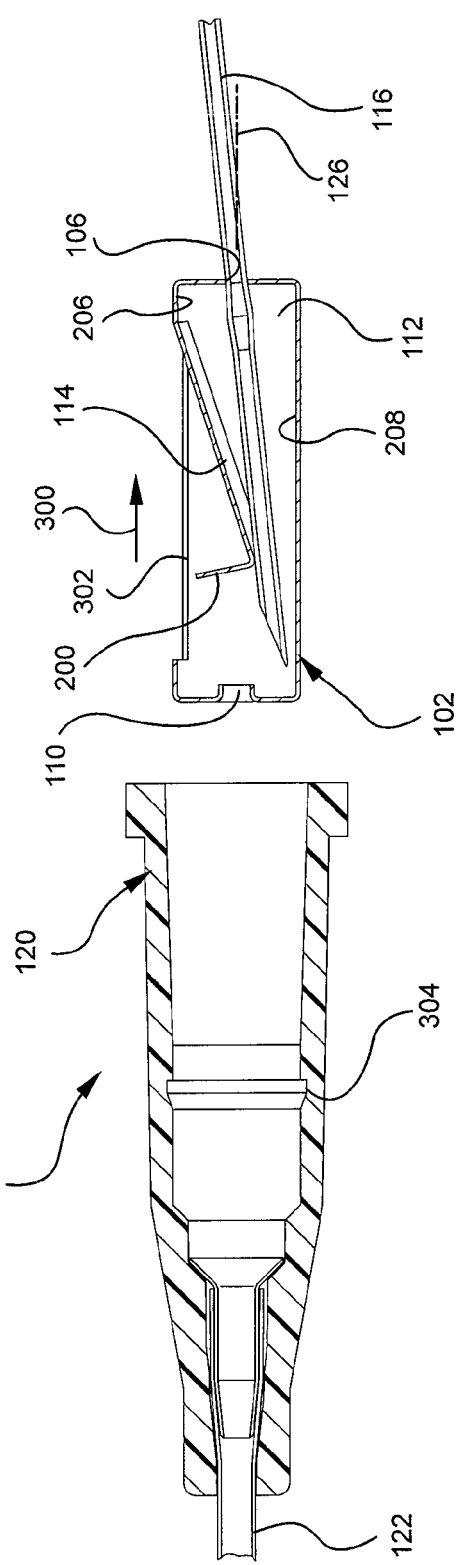
FIG. 3 is a cross-sectional view of the intravenous catheter assembly of FIG. 2 illustrating retraction of the needle through the distal opening into the hollow interior region of the housing.

Referring now to FIGS. 2 and 3, the housing 102 may include a biasing member 114 to apply a force to the needle 116. The force may be oriented to displace the needle relative to the longitudinal axis 126 upon retracting the needle tip 118 through the distal opening 110 and into the hollow interior region 112. In this manner, the needle tip 118 may be effectively and reliably secured within the hollow interior region 112.

In one embodiment, for example, the biasing member 114 may be substantially elongate, with one end 202 coupled to an interior wall 206 of the housing 102. A second end 204 of the biasing member 114 may be biased against the needle 116, where the needle 116 extends between the proximal and distal openings 106, 110 along the longitudinal axis 126. Retracting the needle tip 118 in a direction 300 through the distal opening 110 into the hollow interior region 112 may cause the biasing member 114 to urge a distal portion of the needle 116, including the needle tip 118, towards an opposite wall 208 of the housing 102. In this manner, the force exerted by the biasing member 114 may effectively retain the needle tip 118 within the hollow interior region 112 of the housing 102 after use.

In some embodiments, the second end 204 of the biasing member 114 may include a latch member 200 extending towards the wall 206 of the housing 102. The latch member 200 may be integrated with the biasing member 114 or coupled thereto. In one embodiment, the latch member 200 may selectively protrude through an opening 302 in the wall 206 of the housing 102 to engage a corresponding aperture 304 in the catheter adapter 120. In this manner, the latch member 200 may secure the catheter adapter 120 to the housing 102.

In other embodiments, the latch member 200 may communicate with the biasing member 114 such that the latch member 200 releases the catheter adapter 120 from the housing 102 upon retracting the needle tip 118 in a direction 300 through the distal opening 110. Accordingly, the biasing member 114 may displace the needle 116 from the longitudinal axis 126 while simultaneously releasing the catheter adapter 120 from the housing 102. In this manner, the needle tip 118 may be effectively confined within the hollow interior region 112 of the housing 102 prior to enabling disassembly of the catheter adapter 120 and housing 102. This feature of the present invention may reduce an incidence of accidental needle sticks, as such needle sticks commonly occur during manipulation and disassembly of the intravenous catheter assembly 100 after use.

Figure 4:
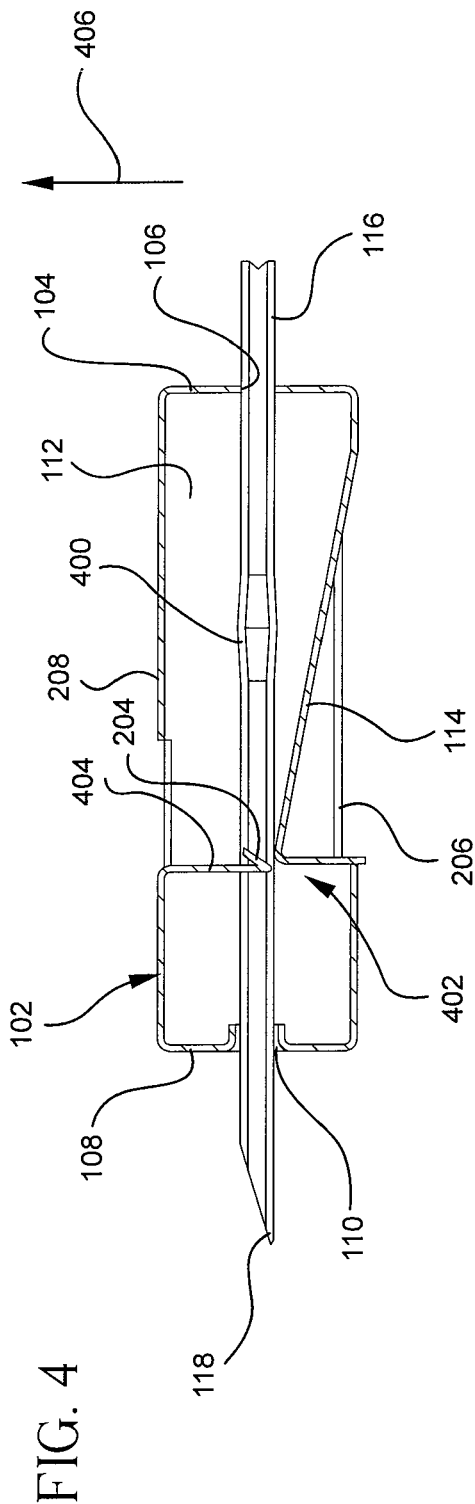
FIG. 4 is a cross-sectional view of one embodiment of a lock feature in a ready position in accordance with the present invention.
Figure 5:
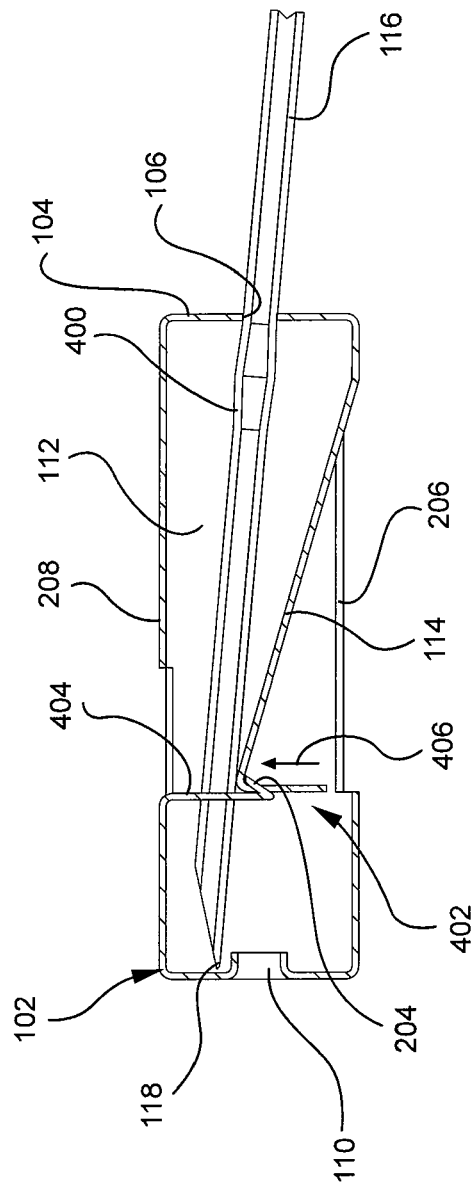
FIG. 5 is a cross-sectional view of the lock feature of FIG. 4 actuated to maintain displacement of the needle relative to the longitudinal axis.
Figure 6:
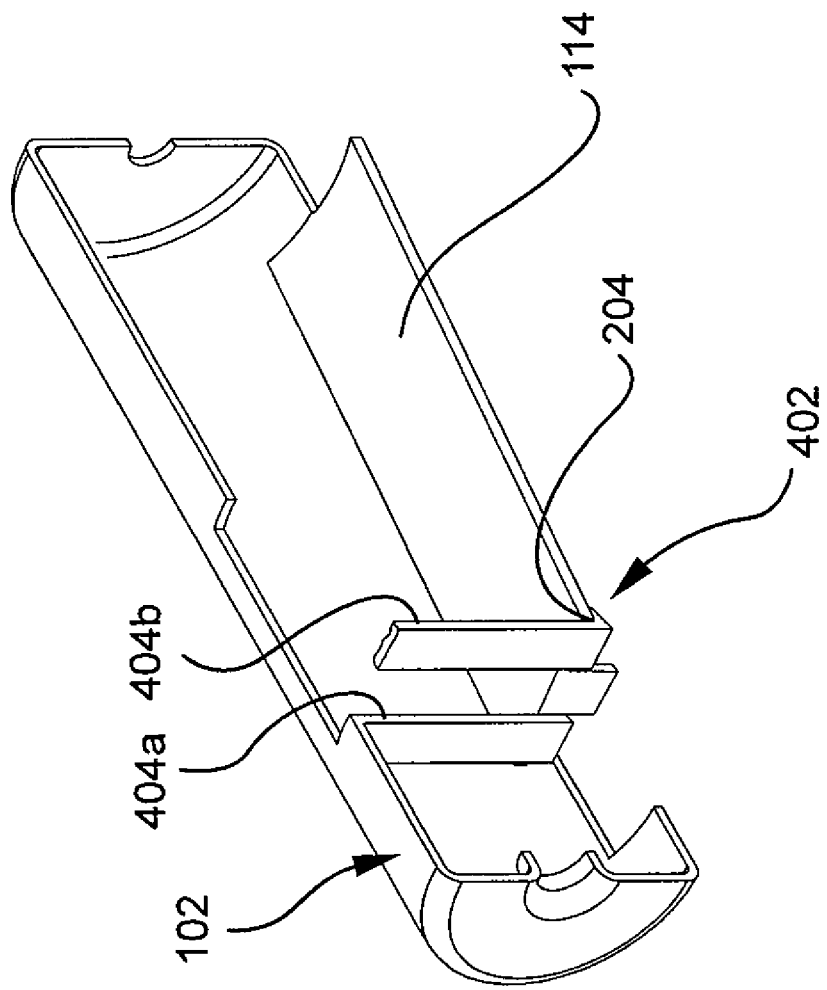
FIG. 6 is a perspective view of the lock feature of FIG. 5.

Referring now to FIGS. 4, 5, and 6, certain embodiments of the present invention include a lock feature 402 to substantially lock a position of the biasing member 114 relative to the hollow interior region 112 to maintain displacement of the needle 116 upon retracting the needle tip 118 through the distal opening 110. The lock feature 402 may include, for example, a hook, a clip, a protrusion, an aperture, or any other suitable device known to those in the art capable of retaining the biasing member 114 in a position to maintain displacement of the needle 116 relative to the longitudinal axis 126.

As shown in FIG. 4, the lock feature 402 may include a hook 404 residing within the hollow interior region 112 and configured to engage at least a portion of the biasing member 114 to maintain displacement of the needle 116. The hook 404 may be attached to an interior wall 208 of the housing 102 substantially opposite the wall 206 supporting the biasing member 114. In some embodiments, the hook 404 may reside substantially adjacent to the second end 204 of the biasing member 114 where the needle 116 extends along the longitudinal axis 126 through the proximal and distal openings 106, 110. In embodiments where the second end 204 includes a latch member 200 or other hook-like feature, the hook 404 and second end 204 may be oriented in opposite directions to substantially face each other where the biasing member 114 is biased against the needle 116 along the longitudinal axis 126.

As previously discussed, retracting the needle 116 through the distal opening 110 may cause the biasing member 114 to move in a direction 406 such that the needle 116 is displaced relative to the longitudinal axis 126. In certain embodiments, the biasing member 114 may continue to urge the needle 116 in this direction 406 until movement of the needle tip 118 is constrained by the wall 208 opposite the wall 206 supporting the biasing member 114. In other embodiments, a resulting position of the needle tip 118 may be intermediate the longitudinal axis 126 and the opposite wall 208.

In any case, movement of the biasing member 114 in this direction 406 may cause the hook 404 to engage the second end 204 of the biasing member 114, thereby preventing movement of the biasing member 114 in a direction towards the supporting interior wall 206 of the housing 102. In this manner, the needle 116 may be locked in a displaced position relative to the longitudinal axis 126 to prevent later re-use.

In some embodiments, as shown in FIG. 6, the hook 404 may include a substantially planar extension coupled to the wall 208 opposite the wall 206 supporting the biasing member 114. The extension may terminate in a bifurcated hook. In other embodiments, the hook 404 may include a pair of parallel hooks coupled to the wall 208 opposite the wall 206 supporting the biasing member 114. In any case, the resulting pair of hooks 404 may be spaced and oriented to engage the second end 204 of the biasing member 114 upon retracting the needle tip 118 through the distal opening 110 and into the hollow interior region 112.

In one embodiment, also depicted by FIG. 6, the biasing member 114 includes a substantially planar extension terminating in a T-shaped cross-section. In other embodiments, the biasing member 114 may be entirely planar, or may include any other cross-sectional shape known to those in the art.

In certain embodiments, the needle 116 may incorporate a securing feature 400 to prevent withdrawing the needle tip 118 through the proximal opening 106 in the housing 102. The securing feature 400 may include a protuberance, a barb, a hook, a crimp, a bulge, or any other feature integrated into or coupled to an outer surface of the needle 116 to create mechanical interference between the proximal opening 106 and the securing feature 400. In other embodiments, the securing feature 400 may include any other feature known to those in the art to prevent withdrawal of the needle tip 118 past the proximal opening 106 in the housing 102.

In some embodiments, the proximal opening 106 may include an inside diameter substantially less than an inside diameter of the distal opening 110. In this manner, the needle 116 may slide substantially freely in a direction towards the catheter 122 to enable the needle 116 to protrude from the end of the catheter 122 to properly introduce the intravenous catheter assembly 100 into a blood vessel. Movement of the needle 116 in an opposite direction 300, however, may be limited by interference between the securing feature 400 and the proximal opening 106. In this manner, the needle tip 118 may be effectively and reliably retained within the housing 102 after use.

Figure 7:
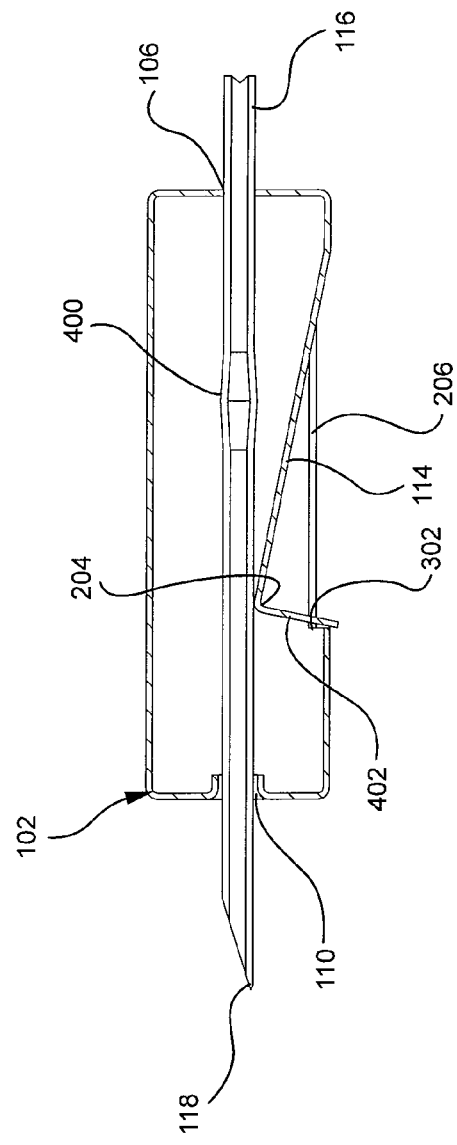
FIG. 7 is a cross-sectional view of an alternative embodiment of a lock feature in a ready position in accordance with the present invention.
Figure 8:
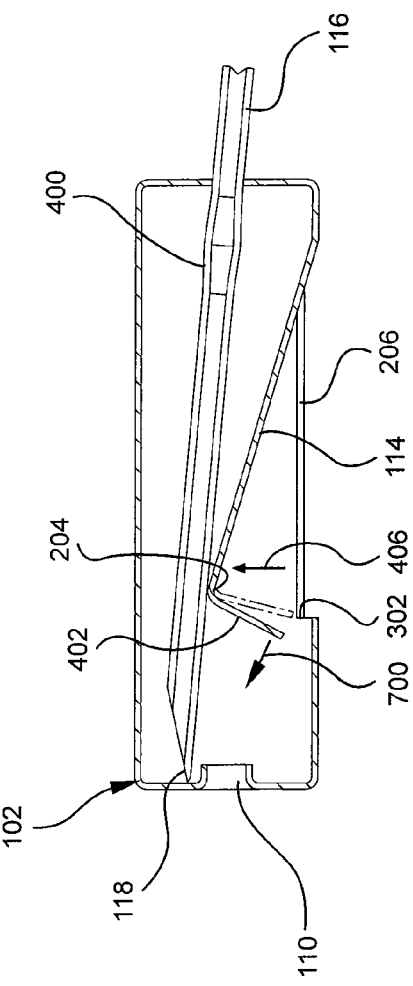
FIG. 8 is a cross-sectional view of the lock feature of FIG. 7 actuated to maintain displacement of the needle to prevent re-use.

Referring now to FIGS. 7 and 8, an alternative embodiment of a lock feature 402 configured to retain the biasing member 114 in a position to maintain displacement of the needle 116 may be integrated into or coupled to a second end 204 of the biasing member 114. Specifically, the lock feature 402 may include a resilient or substantially rigid material extending from the second end 204 of the biasing member 114. The lock feature 402 and biasing member 114 may be substantially unitary in nature, having a flexure bearing, living hinge, or other such feature therebetween to permit the lock feature 402 to flex inwardly towards the biasing member 114 to generate spring energy. Alternatively, the lock feature 402 may be hingedly coupled to the biasing member 114, or may be attached by any other suitable means or device known to those in the art.

The spring energy generated by flexing the lock feature 402 inwardly toward the biasing member 114 may be stored by, for example, providing an opening 302 integrated into the wall 206 supporting the biasing member 114 to engage an end of the lock feature 402 in its flexed state. The opening 302 may include an aperture or notch integrated into the wall 206 and molded to retain the lock feature 402, or may include a channel permitting the lock feature 402 to extend partially or completely therethrough, as discussed in more detail below. Alternatively, such spring energy may be stored by any other retaining device or feature known to those in the art capable of retaining the lock feature 402 in a flexed state relative to the biasing member 114.

As previously discussed, retracting the needle tip 118 through the distal opening 110 into the hollow interior region 112 may cause the biasing member 114 to urge the needle 116 in a direction 406 towards an opposite wall 208 of the housing 102. This movement may simultaneously actuate the lock feature 402 by releasing the lock feature 402 from the opening 302 or other retaining device or feature. Upon release, the lock feature 402 may spring in a direction 700 away from the biasing member 114, thereby preventing re-engagement of the lock feature 402 with the opening 302. In this manner, the lock feature 402 may reliably maintain the needle 116 in a displaced position relative to the longitudinal axis 126.

In some embodiments, the lock feature 402 and latch member 200 may constitute a single element, referred to hereinafter simply as the lock feature 402, that performs a dual function in maintaining displacement of the needle 116 relative to the longitudinal axis 126 in addition to securing the catheter adapter 120 to the housing 102. For example, in certain embodiments, as briefly described above, the lock feature 402 may extend from the biasing member 114 and engage a channel 302 permitting the lock feature 402 to extend therethrough. The lock feature 402 may then engage an aperture 304 in the catheter adapter 120 to secure the catheter adapter 120 to the housing 102.

Retracting the needle tip 118 in a direction 300 through the distal opening 110 may cause the biasing member 114 to urge the needle 116 towards the opposite wall 208, thereby releasing the attached lock feature 402 from the aperture 304 in the catheter adapter 120. Likewise, as previously discussed, retraction of the needle tip 118 through the distal opening 110 may release the spring energy stored by the lock feature 402 such that the lock feature 402 springs away from the biasing member 114 in a direction 700 to prevent re-engagement of the lock feature 402 with the channel 302. This embodiment of the present invention may thus simplify a process for effectively securing the catheter adapter 120 to the housing 102, as well as for maintaining displacement of the needle 116 relative to the longitudinal axis 126 by preventing re-engagement of the lock feature 402 with the channel 302.

Figure 9:
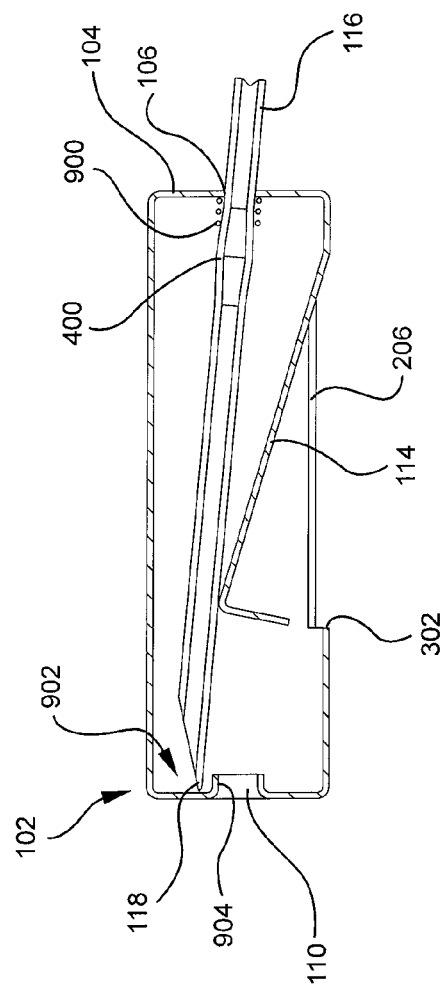
FIG. 9 is a cross-sectional view of one embodiment of a retention element and urging element in accordance with the present invention.
Figure 10:
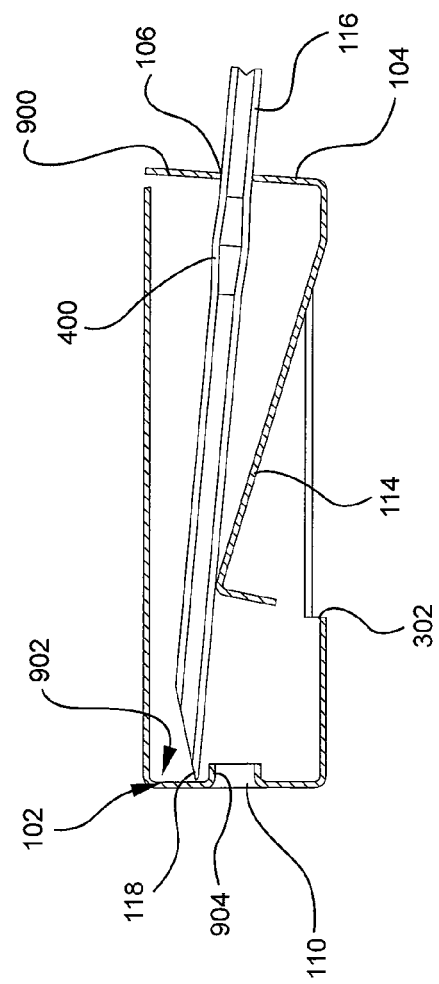
FIG. 10 is a cross-sectional view of an alternative embodiment of an urging element in accordance with the present invention.

Referring now to FIGS. 9 and 10, certain embodiments of the present invention may incorporate an urging element 900 to cooperate with a retention element 902 to provide increased protection against accidental needle sticks and needle 116 re-use. A retention element 902 may include a lip or other feature integrated into the housing 102 to limit movement of the needle tip 118 following displacement of the needle 116 from the longitudinal axis 126. In one embodiment, for example, a retention element 902 includes a substantially enclosed region created by a shoulder 904 extending inwardly from the distal opening 110 towards the hollow interior region 112. The shoulder 904 may include a length sufficient to enable the needle tip 118 to enter the substantially enclosed region, while providing mechanical interference with the needle tip 118 after entry.

An urging element 900 may communicate with the needle 116 to urge the needle tip 118 into the retention element 902 after displacement of the needle 116 from the longitudinal axis 126. For example, in one embodiment, as shown in FIG. 9, the urging element 900 may include a spring or other biasing element or device communicating with the needle 116 between the securing element 400 thereof and the proximal opening 106 of the housing 102. When the needle 116 is retracted in a direction 300 towards the proximal opening 106, the urging element 900 may generate spring energy as it becomes increasingly compressed between the securing element 400 and the proximal opening 106.

In another embodiment, as shown in FIG. 10, the urging element 900 may be integrated into the proximal end 104 of the housing 102. Specifically, the proximal end 104 may be attached to one or more walls 206, 208 of the housing 102 such that the proximal end 104 may selectively flex with respect thereto. For example, the proximal end 104 may include a resilient material, an elastomeric material, or any other suitable material known to those in the art, and may be coupled to at least one wall 206, 208 of the housing 102 such that the proximal end 104 may be substantially biased with respect thereto. In this manner, the needle 116 may be retracted in a direction 300 towards the proximal opening 106 such that the securing feature 400 of the needle 116 interfaces with the proximal end 104. Continued retraction of the needle 116 in the direction 300 may cause the proximal end 104 to flex with respect to at least one wall 206, 208 of the housing 102 to generate spring energy.

In either embodiment, upon further retraction of the needle 116 in the direction 300, the needle tip 118 may reach a position unrestrained by the distal opening 110, and in some cases, beyond the shoulder 904 of the retention element 902. At this point, the urging element 900 may release the stored spring energy to urge the needle 116 in a direction towards the distal opening 110. As this unrestrained position also actuates the biasing element 114, however, the combined movement of the biasing element 114 and urging element 900 may urge the needle tip 118 forward in a direction displaced from the longitudinal axis 126, towards the retention element 902. The retention element 902 may then act to restrain the needle tip 118 by mechanically interfering with its re-alignment with the longitudinal axis 126. Subsequent movement of the needle 116 in any direction may be limited by the combined forces and interactions between the needle 116 and the retention element 902, urging element 900, securing element 400, and biasing element 114.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An apparatus comprising:
a needle tip shield housing defining an inner region, the needle tip shield housing having a distal opening and a proximal opening and a central axis extending between the distal and proximal openings;
a biasing member extending from the needle tip shield housing and having a latch extension, the biasing member and the needle tip shield housing being a single-piece structure;
the latch extension extending away from the central axis toward the exterior of the needle tip shield housing, the latch extension being shaped and sized to engage an aperture in a catheter adapter to secure the needle tip shield housing to the catheter adapter; and
the biasing member, in a single action, displacing a needle away from the central axis and disengaging the latch extension from the aperture in the catheter assembly when the needle is drawn proximally along the central axis so that the tip of the needle is drawn through the distal opening.

2. The apparatus of claim 1, wherein the catheter adapter receives at least a portion of the needle tip shield housing and directs the needle into a catheter extending from the catheter adapter.

3. The apparatus of claim 1, wherein the latch extension selectively protrudes through an opening in the needle tip shield housing to engage the aperture in the catheter adapter.

4. The apparatus of claim 1, further comprising a lock feature to substantially lock a position of the biasing member relative to the inner region to maintain displacement of the needle after the needle is displaced away from the central axis.

5. The apparatus of claim 4, wherein the lock feature comprises a hook disposed within the interior region.

6. The apparatus of claim 4, wherein the lock feature is integrated with the biasing member such that the lock feature selectively abuts a wall of the hollow interior region to maintain displacement of the needle.

7. The apparatus of claim 1, wherein the needle comprises a securing feature to prevent withdrawing the tip of the needle through the proximal opening.

8. The apparatus of claim 1, wherein the inner region comprises a retention element to retain the end of the needle in a position displaced from the longitudinal axis upon retracting the end of the needle through the distal opening.

9. The apparatus of claim 8, further comprising an urging element communicating with the needle that urges the tip of the needle into a position retained by the retention element after the needle is displaced away from the central axis.

10. The apparatus of claim 1, further comprising an extension coupled to the distal opening of the needle tip shield housing and extending into the interior region of the needle tip shield housing, and further comprising a retention space between the extension and the needle tip shield housing.

11. The apparatus of claim 10, wherein the needle comprises a securing feature disposed on the needle, the securing feature preventing the tip of the needle from being withdrawn through the proximal opening of the needle tip shield housing.

12. The apparatus of claim 11, further comprising an urging element disposed between the securing features and the needle when the needle securing feature drawn toward the proximal opening of the needle tip shield housing, the urging member urging the securing feature distally away from a distal end of the needle tip shield housing.

13. A method to automatically secure an end of a needle after contact with a blood vessel, the method comprising:
providing a catheter adapter, the catheter being directly coupled to a catheter;
providing a needle tip shield housing within an interior lumen of the catheter adapter, the needle tip shield having a proximal end, a distal end, and a hollow interior region extending therebetween;

integrating into the proximal end a proximal opening and into the distal end a distal opening, wherein the proximal opening and distal opening are configured to receive a needle therethrough along a longitudinal axis;

coupling to the needle tip shield housing a biasing member having a latch extension, the biasing member and the needle tip shield housing being a single-piece structure;

extending the latch extension away from the longitudinal axis into an aperture in the interior lumen of the catheter adapter to secure the needle tip shield housing to the catheter adapter; and in a single action, displacing a needle away from the central axis and disengaging the latch extension from the aperture in the catheter assembly when the needle is drawn proximally along the central axis so that the tip of the needle is drawn through the distal opening.

14. The method of claim 13, further comprising inserting the needle through the proximal and distal openings along the longitudinal axis.

15. The method of claim 13, further comprising providing a catheter adapter to receive at least a portion of the needle tip shield housing and direct the needle into a catheter extending from the catheter adapter.

16. The method of claim 15, further comprising securing the catheter adapter to the needle tip shield housing via a latch member.

17. The method of claim 13, further comprising providing a lock feature communicating with the biasing member to substantially lock a position of the biasing member relative to the hollow interior region upon retracting the end of the needle through the distal opening.

18. A intravenous catheter assembly comprising:
a catheter adapter having an interior lumen therein, the interior lumen having an inner surface, the catheter adapter being directly coupled to a catheter;
an aperture formed on the inner surface;
a needle tip shield housing defining an inner region, the needle tip shield housing having a distal opening and a proximal opening and a central axis extending between the distal and proximal openings;
a biasing member of the needle tip shield housing and having a latch extension, the biasing member and the needle tip shield housing being a single-piece structure;
the latch extension extending away from the central axis toward the exterior of the housing, the latch extension being shaped and sized to engage an aperture in the catheter adapter to secure the housing to the catheter adapter; and
the biasing member, in a single action, displacing a needle away from the central axis and disengaging the latch extension from the aperture in the catheter assembly when the needle is drawn proximally along the central axis so that the tip of the needle is drawn through the distal opening.

19. The intravenous catheter assembly of claim 18, wherein the catheter assembly includes an inner bore that receives the housing, and wherein the aperture is disposed on the inner bore.

* * * * *